United States Patent [19]

Kingsley et al.

[11] Patent Number: 5,523,474
[45] Date of Patent: *Jun. 4, 1996

[54] TEREPHTHALIC ACID PRODUCTION USING EVAPORATIVE COOLING

[75] Inventors: Jeffrey P. Kingsley, Newburgh; Anne K. Roby, Peekskill, both of N.Y.

[73] Assignee: Praxair Technology, Inc., Danbury, Conn.

[*] Notice: The term of this patent shall not extend beyond the expiration date of Pat. No. 5,371,283.

[21] Appl. No.: 241,438

[22] Filed: May 11, 1994

[51] Int. Cl.$^6$ .................................................. C07C 51/16
[52] U.S. Cl. ........................................ 562/416; 422/225
[58] Field of Search ........................................... 562/416

[56] References Cited

U.S. PATENT DOCUMENTS

| | | | |
|---|---|---|---|
| 4,243,636 | 1/1981 | Shiraki | 562/416 |
| 4,370,496 | 1/1983 | Shigeyasu | 562/416 |
| 4,827,025 | 5/1989 | Shiraki | 562/416 |
| 4,855,492 | 8/1989 | Hundley | 562/416 |
| 4,900,480 | 2/1990 | Litz et al. | 261/36.1 |
| 5,004,830 | 4/1991 | Park | 562/416 |
| 5,371,283 | 12/1994 | Kingsley | 562/416 |

*Primary Examiner*—Michael L. Shippen
*Attorney, Agent, or Firm*—Alvin H. Fritschler

[57] ABSTRACT

The oxidation of p-xylene to produce terephthalic acid is carried out using pure or nearly pure oxygen and evaporative cooling. By-product and waste generation are reduced, oxygen utilization is enhanced, desirable operating conditions are employed, and the need for direct contact heat exchange surfaces in the reactor vessel is obviated.

12 Claims, 2 Drawing Sheets

TEREPHTHALIC ACID PRODUCTION USING EVAPORATIVE COOLING

BACKGROUND OF THE INVENTION

1. Field of the Invention

This invention relates to the production of terephthalic acid. More particularly it relates to an enhanced process and system for the production of said terephthalic acid.

2. Description of the Prior Art

In a typical air or enriched air based process for producing terephthalic acid, liquid p-xylene is fed to a stirred tank reactor, with a monobasic aliphatic acid, typically acetic acid being used as a solvent. The ratio of solvent to reactant is typically one to ten weights of solvent per volume of reactant (1:1 to 10:1). The reaction is catalyzed with a heavy metal or mixture of heavy metals, most commonly cobalt and manganese in the form of acetate salts. In addition, bromine, in the form of bromic acid, is commonly used as an initiator. The reactor is maintained at an operating temperature of between 170° C. and 225° C. The operating pressure is generally between 100 and 300 psig. Compressed air or enriched air, typically having between 21% and 28% oxygen, is sparged into the bottom of the reactor. Oxygen from the air is dissolved into the liquid phase and reacts with the p-xylene to produce the desired terephthalic acid product. Intermediate oxidation products and by-products are also formed in quantities that depend on the reaction conditions employed. At a residence time of one hour, the conversion of p-xylene is typically about 99%, with the yield to desired terephthalic product being greater than 96%.

The most important intermediate oxidation product in the production of terephthalic acid (TPA) is 4-carboxybenzaldehyde (4-CBA), which is one oxidation step removed from terephthalic acid. The presence of 4-CBA in the TPA produce is undesirable. It acts as a chain terminator in subsequent polymerization reactions which convert TPA to its most important end products, i.e., polyester fibers and polyethylene terephthalate resins. For a given residence time, the conversion of 4-CBA to TPA has been observed to increase with temperature. Hence, the concentration of 4-CBA in the TPA product decreases with increased operating temperature, so that TPA product quality increased at higher operating temperatures.

Raw material losses to undesirable byproducts, on the other hand, also increase with temperature. The acidic acid solvent and, to a lesser extent, p-xylene, react to produce carbon dioxide, carbon monoxide, methyl bromide and methyl acetate, all of which are environmentally sensitive materials. Since a high reaction temperature must be maintained to make product terephthalic acid that meets applicable quality standards, the loss of acetic acid and the commensurate production of byproduct gases is usually a significant factor in the economics of the overall operation.

In such known operations, feed air must be compressed to a pressure somewhat above the reactor operating pressure before it is blown into the reactor through a pipe or other submerged sparger. The air bubbles are dispersed in the reactor and are circulated through the body of liquid reactant and solvent by an agitator device. The oxygen concentration in the air bubbles decreases as the oxygen dissolves and reacts with the p-xylene. The residual air bubbles disengage from the liquid phase and collect in a gas space at the top of the reactor to form a continuous gas phase. This waste gas must be vented in order to provide space for fresh air feed, while maintaining adequate gas hold-up in the reactor to promote the desired oxygen transfer from the air to the liquid phase.

To avoid the possibility of fire or explosion, the oxygen concentration in the gas space at the top of the reactor must be maintained below the flammable limit. For practical operating purposes, the oxygen concentration must be maintained at less than 8–9% by volume. More typically, the oxygen concentration in the gas space is maintained below 5% by volume to provide a safe margin below the flammable limit. Thus, in a well stirred tank reactor, the average concentration of oxygen in the circulating air bubbles must be below 5% in order to insure that the average concentration of oxygen in the gas that collects in the headspace of the reactor is nonflammable.

The oxygen concentration in the gas space is a function of the rate at which air or enriched air is fed into the reactor and the rate of consumption of oxygen from the air by reaction with p-xylene. The rate of reaction and, therefore, the TPA production rate per unit of reactor volume, increases with temperature, pressure, oxygen concentration in the gas phase, p-xylene concentration, promoter concentration and catalyst concentration. Since the concentration of dissolved oxygen in the liquid phase, and, hence, the reaction rate of oxygen, is proportional to the oxygen concentration in the gas phase, for a given set of reaction conditions, the 5% oxygen restriction in the headspace effectively limits the oxygen reaction rate.

Clearly, air or said enriched air, typically 21% to 28% oxygen, based TPA plant design requires optimization of temperature, pressure, catalyst loading, air feed rate, reactor volume, and vent gas treatment equipment. For example, increasing temperature increases productivity per unit reactor volume and improves product purity, but it also leads to yield and solvent losses, and byproduct gas formation due to over oxidation.

It has more recently been proposed to use oxygen, or nearly pure oxygen, as an oxidant in the TPA production process. Such an oxygen based process for TPA production would typically be carried out in a conventional reaction vessel employing direct contact cooling devices, for example cooling coils, to remove the heat of reaction from the vessel and to maintain the desired operating temperature. Such oxygen based TPA production, carried out in a reactor adapted to obviate the potential for fire or explosion, would desirably be carried out under TPA operating conditions serving to minimize the amount of undesired by-products present in the terephthalic acid product and the amount of vent gases to be treated as part of the overall production operation.

In the commercial practice of otherwise desirable oxygen based terephthalic acid production operations, as in conventional air based TPA operations, a disadvantageous feature is occasioned by the fact that the desired TPA product of p-xylene oxidation is a solid product. As a result, the reaction mixture is supersaturated with TPA, and the solid TPA reaction product readily precipitates onto any cooled surface. Consequently, the cooling coils typically used for the direct cooling of the reactor to the desired operating temperature rapidly become coated with the solid TPA product and lose much of their heat transfer capability. This results in premature shut-down of the TPA production operation for maintenance purposes, adding considerably to the overall costs associated with TPA production.

As the production of TPA is a highly significant commercial operation, there is a genuine need in the art for an improved TPA process and system. In particular, the loss of important TPA production time due to the above-indicated heat transfer problems must be overcome to enhance the overall efficiency of the TPA process and system. As oxygen based TPA production operations are particularly desirable, such improvement in the art needs to be applicable to oxygen based TPA operations so as to enhance the feasibility of their use in preference to conventional air based TPA production operations.

It is an object of the invention, therefore, to provide an improved process and system for the production of terephthalic acid.

It is another object of the invention to provide an improved oxygen based TPA production process and system.

It is a further object of the invention to provide a process and system for TPA production obviating the need for premature shut-down because of the loss of heat transfer capability and cooling effectiveness upon precipitation of the TPA product.

With these and other objects in mind, the invention is hereinafter described in detail, the novel features thereof being particularly pointed out in the appended Claims.

SUMMARY OF THE INVENTION

The oxidizing reaction to produce terephthalic acid is carried out using oxygen in place of air and a gas-liquid mixing process and system enhancing the consumption of oxygen and providing for evaporative cooling to remove the heat of reaction, obviating the need for direct contact cooling means in the reactor vessel.

BRIEF DESCRIPTION OF THE DRAWINGS

The invention is hereinafter further described with reference to the accompanying drawings in which.

DETAILED DESCRIPTION OF THE INVENTION

Figure 1:
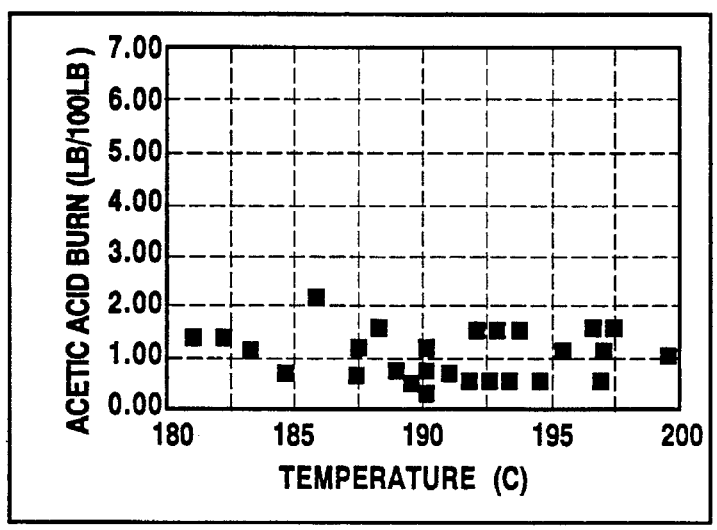
FIG. 1 is a plot of acetic acid solvent burn as a function of temperature in the evaporatively cooled process of the invention.

The objects of the invention are accomplished by carrying out the desired terephthalic acid production, using oxygen in place of air, in a manner enabling evaporative cooling to be employed, particularly through the advantageous use of a modified, highly desirable Liquid Oxidation Reactor (LOR) process and system. While the TPA product is obtained in the solid phase, the invention avoids the practical operating problems associated with the common use of direct cooling heat exchange surfaces for removing the heat of the oxidation reaction that result from TPA and other solids precipitation on the heat transfer surfaces of cooling coils and the like. Thus, the safe and efficient use of pure or nearly pure oxygen for the p-xylene oxidation reaction can conveniently be carried out using evaporative cooling to remove the heat of reaction generated during the oxidation reaction.

The LOR process and system, as employed in the practice of the invention, enables oxygen to be used instead of air, while obviating the potential for fire or explosion, under desirable operating conditions serving to minimize the amount of undesired byproducts present in the terephthalic acid product. In addition, the amount of vent gas to be treated is minimized. Furthermore, the invention can be carried out at lower operating temperatures and/or pressures than are typically employed in conventional air based processes, while achieving equivalent TPA production. Undesired reactions that consume solvent and reactant, and produce byproduct gases, are suppressed at the modest operating temperature conditions conveniently used in the practice of the invention.

In the LOR process and system as described in the Litz et al. patent, U.S. Pat. No. 4,900,480, oxygen and the body of liquid are mixed and recirculated without appreciable loss of oxygen to the overhead gas phase. In the practice of the FIG. 3 embodiment of the invention, oxygen is largely consumed in the first pass through the downward pumping helical impeller/draft tube combination positioned within the reactor vessel, and within the roll cells referred to below. As a result thereof and of the modified system configuration employed in desirable embodiments of the invention, the recirculation of oxygen and other gas bubbles through the draft tube is minimized.

One of the important advantages of the modified LOR approach of the invention is that, since the gas-liquid reaction mixture is pumped from the draft tube positioned near the bottom of the reactor vessel at high velocities, thereby forming a jet that entrains surrounding fluid outside the draft tube and that impacts the bottom of the reactor vessel, thereby setting up roll cells in said reaction mixture in the bottom portion of the reactor. These roll cells essentially trap the dispersed gas phase until it is either completely consumed or coalesces to a critical bubble diameter having sufficient buoyancy to rise through the liquid and escape. This pattern of fluid dynamics yields very high oxygen use efficiency even in a single pass through the impeller positioned in the draft tube.

The process conditions for the oxidation of organic compounds in the modified LOR system of the invention will generally be within the range of those practiced commercially in air based oxidation processes. The most significant difference is that, for a given reaction mixture and operating temperature, the operating pressure of the reactor will be lower with the oxygen based process than with the air based process.

It will be noted that the optimal process conditions, such as operating temperature and catalyst concentration, may be different for the oxygen based p-xylene oxidation reaction than for the corresponding air based reaction. The air based process economics are determined by the relative benefits of high temperature on reaction rate and conversion compared with the increased loss of product selectivity and yield with increased operating temperature conditions. Such loss of selectivity is seen in the increased loss of solvent and/or reactant to waste byproducts, such as carbon dioxide or carbon monoxide. Catalyst concentration can have a similar effect on reaction rate as well as selectivity. With the evaporatively cooled oxygen based process as practiced in accordance with the invention, product conversion and reaction rate are found to increase with increasing operating temperature, but no dependance of solvent loss on reaction temperature has been observed.

With reference to FIG. 1 of the drawing, the acetic acid solvent acid burn behavior, illustrated as a function of temperature, relates to the oxidation of p-xylene to terephthalic acid in the evaporatively cooled process of the invention. Those skilled in the art will appreciate that the reaction of acetic acid solvent is undesired, and is found to be consistently low at typical reaction temperatures ranging from about 180° C. to 200° C. The indicated data was taken in a 3.3L LOR reactor modified in accordance with the invention. The inside diameter of the reactor was 5 inches, and both a 2 inch impeller and a 3 inch impeller were positioned inside a draft tube and were used at a rotational speed of 1,000 rpm, said draft tube being positioned in the reactor as described and claimed herein. The feed mix was typically 11% p-xylene. The reaction catalysts employed were cobalt and manganese, as acetate salts, ranging in concentrations of from 200 to 2,000 ppm, and from 500 to 3,000 ppm, respectively. Bromine, in the form of hydrogen bromide, was used as an indicator with concentrations in the feed mix ranging from 400 to 3,000 rpm.

Figure 2:
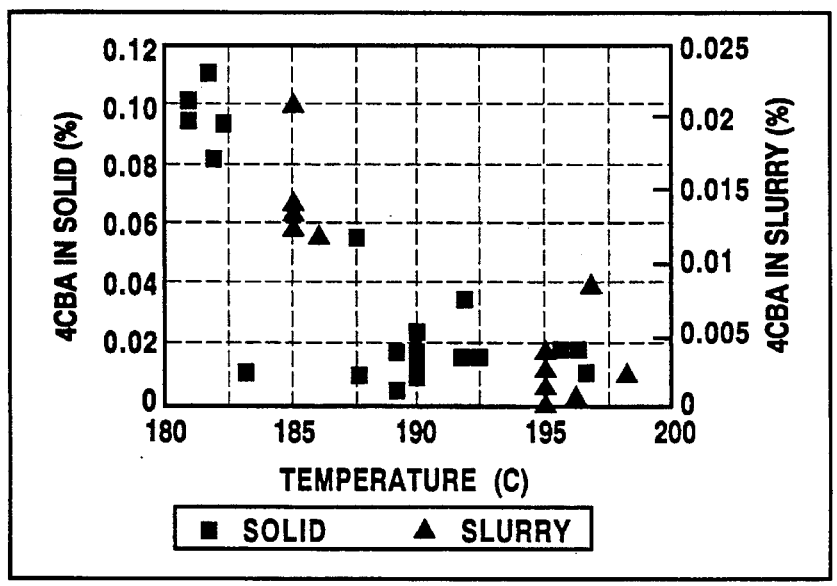
FIG. 2 is a plot of the concentration of 4-CBA intermediate product in the solid and slurry products of p-xylene oxidation with pure oxygen as a function of temperature in the evaporatively cooled process of the invention.

FIG. 2 of the drawings illustrates the concentration of 4-CBA in the solid and slurry products of p-xylene oxidation with pure oxygen, as a function of temperature in the evaporatively cooled process of the invention. It will be seen that, in both the slurry and the solid product, the undesired concentration of 4-CBA decreases as the temperature increases into the desirable temperature conditions of the invention.

For the subject oxygen based, evaporatively cooled TPA process, therefore, product quality increases with temperature, but solvent loss has been found to be insensitive to temperature increases in the desirable range employed in the practice of the invention.

Figure 3:
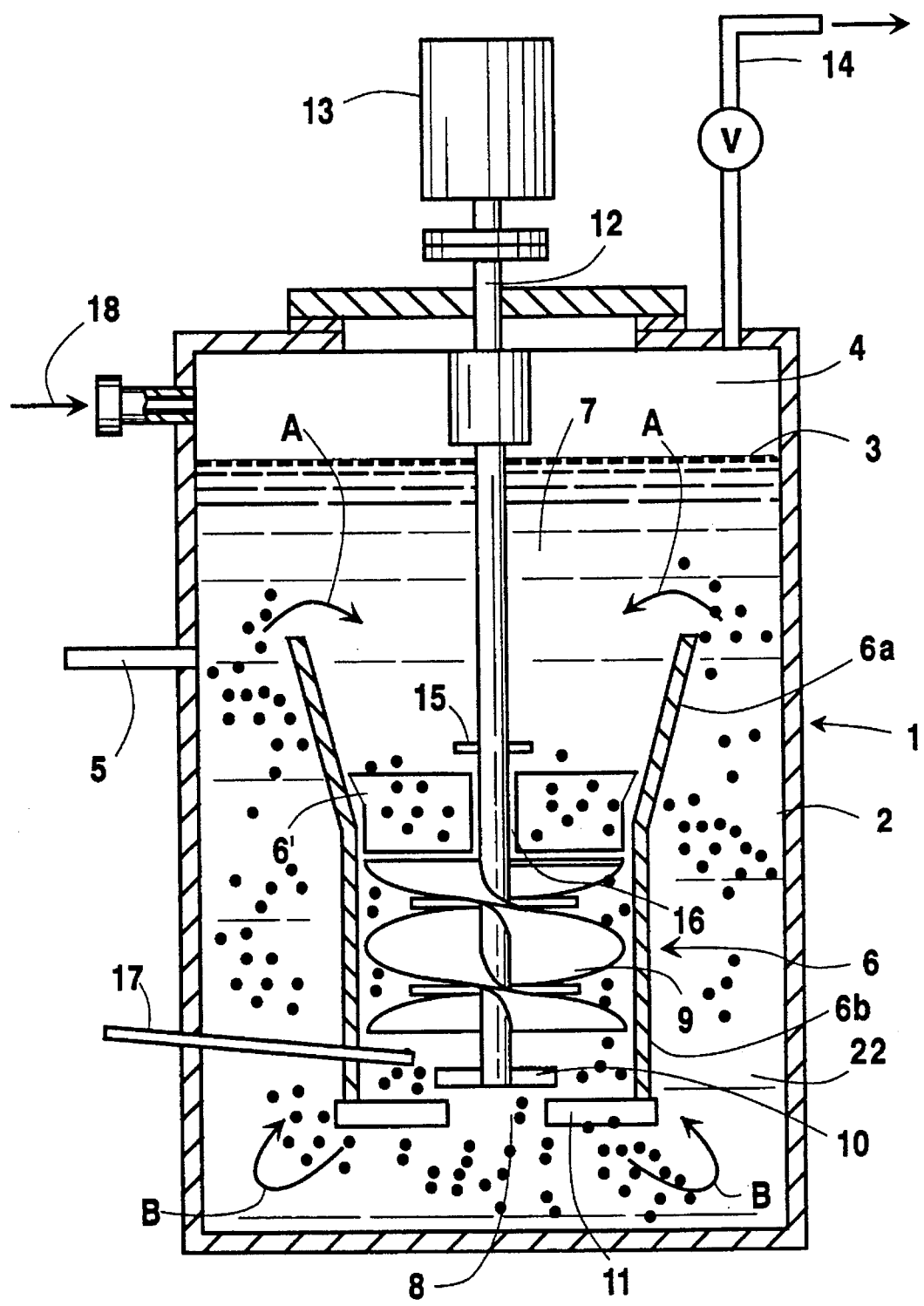
FIG. 3 is a schematic side elevational view of an oxygen-p-xylene reactor vessel representing a desirable embodiment of the invention.

FIG. 3 of the drawings illustrates a modified LOR system suitable for use in accordance with the invention for the oxidation of p-xylene with pure or nearly pure oxygen, using evaporative cooling of the reaction mixture. In this embodiment, reactor vessel 1 has a body of organic liquid 2 therein, with gas-liquid interface 3 and overhead gas phase 4. Product liquid is removed from reactor vessel 1 through line 5. As in LOR system of Litz et al., hollow draft tube 6 is typically centrally positioned within reactor vessel 1, with open end 7 at the top and open end 8 at the bottom thereof. Impeller means 9 are positioned within hollow draft tube 6. Such impeller means 9 are downward pumping helical impeller means adapted to facilitate the downward flow of liquid at high velocity from said body of liquid 2 in hollow draft tube 6, the formation of turbulent roll cells B, and upward flow of said liquid therefrom in the annulus between the side wall of the reactor vessel and the outside of hollow draft tube 6 above said roll cells B. Impeller means 9 commonly include radial flow impeller means 10 and, if desired, lower baffle means 11 to facilitate the desired recirculating flow of liquid in reactor vessel 1. A suitable drive shaft 12 that extends upward from reactor vessel 1 for connection to suitable driving means 13 used to operate impeller means 9.

In FIG. 2 of the Litz et al. patent referred to above, it will be noted that hollow draft chamber 29 optimally includes a conically flared portion 30a at the upper end thereof for purposes of facilitating the flow of a gas bubble-liquid mixture into the draft chamber for downward passage therein. In the modified LOR system of the invention, a conically flared portion is likewise positioned at the upper end of the hollow draft tube 6, but the configuration of said conically flared portion is quite different than that of Litz et al., and it is used for the opposite purpose of reducing the amount of gas bubbles drawn downward into hollow draft tube 6. Thus, vertically elongated, conically flared portion 6a of hollow draft tube 6 extends upward above the generally cylindrical bottom portion 6b thereof in which impeller means 9 is positioned. The increase in diameter at the top of said conically flared portion 6a serves to minimize the downward velocity of liquid flow pattern A across the top of said hollow draft tube 6, thereby appreciably reducing the portion of the gas bubbles rising in the reactor vessel outside said hollow draft tube 6 that are drawn down into impeller means 9 with the downward flow of reactant liquid in hollow draft tube 6. For this purpose, vertically elongated, conically flared upper portion 6a extends in vertical distance from about 0% to about 20%, preferably about 100% to about 150%, of the length of the bottom portion 6b of said hollow draft tube, in which impeller means 9 are positioned, and which is typically of cylindrical, nontapered configuration. The diameter at the top of said draft tube, i.e., the enlarged diameter at the top of upper portion 6a, is appropriately sized to minimize the downward velocity of liquid across the top of the draft tube, e.g., to about 1.5 ft./sec. in certain embodiments. While the dimensions of said upper portion 6a of draft tube 6 will be understood to vary depending on the overall circumstances of a given application, a clearance of from about 0.5 to about 4.0 times the diameter of the draft tube will typically pertain between said upper portion 6a and the walls of the reaction vessel. In some instances, the enlarged diameter of upper portion 6a will be from 1.5 to 3.0 times the diameter of hollow portion 6b. In particular embodiment's, the enlarged diameter at the top of upper portion 6a will be from about 40% to about 80% of the inside diameter or width of reactor vessel 1, preferably from about 50% to 60% thereof. The geometry and rotational speed of the impeller means are factors in determining the size of draft tube 6, and upper portion 6a thereof, for a particular application. The high velocity of the liquid pumped downward through the impeller means will typically be in the range 5 or 6 to about 8 ft./sec. or more, such as to create the high turbulent rolls cells that trap undissolved oxygen and enhance the desired dissolution thereof. Baffle means 6' is also desirably positioned in said conically flared portion 6a of hollow draft tube 6 to facilitate the downward flow of liquid to impeller means 9.

As a result of the rapid consumption of feed oxygen upon injection into hollow draft tube 6, and the minimizing of the downward flow of liquid across the top of said draft tube, the modified LOR impeller/draft tube combination of the invention effectively reduces the amount of recirculated gas passing downward in the draft tube. The gas bubbles passing upward in liquid flow pattern B in the reaction vessel outside bottom portion 6b of the hollow draft tube comprise principally volatile organic chemicals (VOCs), reactant solvent, water vapor and by products, such as CO and $CO_2$, with only small amounts of undissolved oxygen being present therein. The evaporation of the volatile organic species provide the evaporative cooling needed to remove the heat of reaction of the desired organic chemical oxidation operation. It will be seen that the gas bubbles rising in reactor vessel 1, particularly in the vicinity of the top of upper portion 6a of hollow draft tube 6, and in the region above the draft tube to gas-liquid interface 3 contain very little, i.e., substantially no, oxygen, so that the oxygen concentration in overhead gas phase 4 is readily maintained within the indicated limits to assure against the possibility of fire or explosion. The region of the body of liquid 2 near the top upper portion 6a of hollow draft tube 6 and in the portion of liquid body 2 above said upper portion 6a thus constitutes, in effect, a relatively quiescent zone of less turbulence analogous to that provided in the LOR process and system of the Litz et al. patent. It will be understood that gases are vented from overhead gas phase 4, through vent means 14, during the oxidation reaction process. For purposes of the invention, it should also be noted that the lower nonflared portion 6b of hollow draft tube 6 is desirably positioned in the lower half of reactor vessel 1, as shown in FIG. 3, preferably near the bottom of said vessel so as to provide impact between the gas bubble-liquid mixture being discharged from the bottom of reactor vessel 1 and the bottom of the reactor vessel.

In furtherance of the entirely different gas flow patterns desired in the practice of the invention vis-a-vis the gas-liquid mixing operation described in the Litz et al. patent, baffle means corresponding to guide baffle means 34, used in the Linz et al. system to direct a gas bubble-liquid mixture to the top of hollow draft chamber 29, are not employed in the practice of the invention. The invention does, however, employ a small horizontal baffle means, i.e. disc 15, positioned in hollow draft tube 6 around drive shaft 12 in the region above the impeller means. Such baffle means serve to preclude the ingestion of gas, by vorex action, from overhead gas phase 4 along said drive shaft 12.

As indicated above, the invention uses pure or nearly pure oxygen for the oxidation of p-xylene, with evaporative cooling being employed to remove the heat of reaction generated by the oxidation reaction. For this purpose, the mass transfer of oxygen from the gas phase to the liquid phase is substantially enhanced so as to increase the overall rate of reaction as compared to air based oxidation reactions. The practice of the invention enables a rapid rate of oxygen consumption to be achieved such that a very high oxygen use efficiency, i.e., at least 75% and preferably 90% or more, is obtained upon first injection of pure or nearly pure oxygen directly into hollow draft tube 6 as herein described. Such pure oxygen utilization, coupled with the configuration of said hollow draft tube 6 as described above, minimizes the recirculation of gas bubbles through said draft tube 6, enables evaporative cooling to be advantageously employed, and precludes undesired cavitation in impeller means 9 that would impede or preclude the desired recirculation of liquid reactant and the breaking up and rapid dispersion of oxygen as fine bubbles in the liquid reactant.

For purposes of the evaporative cooling approach of the invention, the pure or nearly pure oxygen feed is added to reactor vessel 1 at a point of high turbulence within hollow draft tube 6 rather than elsewhere in the body of organic liquid 2. While oxygen addition can be made at any convenient point of high turbulence in said hollow draft tube 6, or just below it, such as, for example, through injection line 16 directly to lower portion 6b thereof immediately below impeller means 9, it is desirable and convenient to inject oxygen into the system, through injection line 17 to a point in said lower portion 6b below helical impeller means 9 and radial flow impeller means 10, such as flat blade turbines, if employed, or to a point in said lower portion 6b between helical impeller means 9 and said radial flow impeller means 10, if employed. It will be appreciated that these are points of high turbulence and that the injection of the oxygen feed at such a point of high turbulence is important to the desired rapid consumption of oxygen. The initially high concentration of oxygen in the gas phase at the point of injection serves to enhance the mass transfer rate of the oxygen into this region of the liquid reactant, which would be otherwise oxygen depleted in the liquid phase due to the rapid rate of the oxidation reaction.

In the practice of the FIG. 3 embodiment of the invention, it will be understood that nitrogen or other inert purge gas can be passed into overhead gas phase 4 through line 18 principally to inert the small amounts of unreacted oxygen that may escape into the overhead gas phase. In this regard, it should be noted that the draft tube configuration is an excellent pump, which sets up the above-indicated roll cells that trap undissolved oxygen, which allows high oxygen efficiency to be achieved and limits the amount of nitrogen or other inert purge gas required in the overhead gas phase compared to the FIG. 4 embodiment discussed below. The roll cells form a very significant portion of the turbulent flow field produced by said impeller means.

In the TPA production operation, a significant amount of organic material and water evaporate from the reaction mixture. The vent gases are desirably cooled, and the condensibles therefrom are returned to the reactor in preferred embodiments of the invention. A portion of the vent flow is desirably diverted for gas analysis of carbon dioxides and oxygen. The oxygen utilization efficiency observed in the practice of the invention for the reaction of p-xylene with oxygen is greater than 99%. That is, less than 1% of the oxygen that is fed to the reactor is vented unreacted.

The relative benefits due to the use of oxygen in accordance with the practice of the invention instead of air in the conventional process for the production of TPA are observed over the range of suitable operating conditions, and the optimal operating conditions for the oxygen-based process of the invention are generally more favorable than those that pertain in the practice of the conventional air based process.

The solvent:reactant ratio is from about 1:1 to about 8:1 on a wt/volume basis in the practice of the invention. The catalyst for the desired oxidation reaction is a mixture of cobalt and manganese, preferably as acetate salts. The catalyst loading should be between 500 and 3,000 ppm, with the ratio of cobalt to manganese being from 0.1 to 10:1, preferably about 3:1 on a weight basis. Bromine is used as an initiator and is added conveniently as hydrogen bromide (HBr). The bromine loading is between 0.1:1 and 1:1 on a weight basis relative to the total catalyst loading, preferably about 0.3:1. The residence time for the liquid is between 30 and 90 minutes. The operating temperature is generally between 150° C. and 200° C. The operating pressure is between 100 psig and 200 psig.

It should be noted that the optimal operating conditions for a specific embodiment of the invention are largely determined by the economics applicable to that embodiment. As indicated above, an increase in operating temperature increases solvent loss and improves product quality. This affect of temperature on these two parameters can be seen from the data presented in FIGS. 1 and 2 of the drawing. FIG. 1 shows the affect of operating temperature on acetic acid burn. FIG. 2 shows the affect of operating temperature on the concentration of 4-CBA in the product. As noted above, as the level of 4-CBA increases, product quality decreases. Based on the data shown in FIGS. 1 and 2, the preferred operating temperature for the practice of the invention has been found to be about 180° C., with the preferred operating pressure being between 130 psig and 150 psig. Thus, desirably milder operating conditions can be employed in the practice of the invention than are generally employed in the practice of the conventional air based process for terephthalic acid production.

In the practice of an illustrative embodiment of the invention using the reactor system shown in FIG. 3, the relative flow rates for major components of the subject oxidation reaction are as follows with the flows being based on 100 lb./minute liquid feed. The liquid feed introduced to the reactor comprises 20 lb p-xylene, 70 lb. acetic acid, 10 lb. water, 0.22 lb. cobalt acetate, 0.08 lb. manganese acetate and 0.02 lb. hydrobromic acid. An oxygen feed of 18.5 lb. provides a liquid product stream of 69 lb. acetic acid, 30.5 lb. terephthalic acid, 17.5 lb. water, 0.22 lb. cobalt acetate, 0.08 lb. manganese acetate, 0.02 lb. hydrobromic acid and 0.08 lb. xylene. A 2 lb. nitrogen purge gas us used, with the vent gas being 2 lb. nitrogen, 1.20 lb carbon dioxide, 0.60 lb. carbon monoxide and 0.23 lb. oxygen.

The undesired production of methyl acetate in the conventional air based TPA production process is reported to be approximately 0.4/100 lb. of TPA produced. In the oxygen based process as described and claimed herein, such methyl acetate production can be decreased very appreciably, with test data indicating that the methyl acetate production can be decreased to less than 0.2 lb./100 lb. of TPA production in particular embodiments of the invention. Production of carbon monoxide and carbon dioxide can likewise be cut by nearly an order of magnitude in the practice of the invention. A similar decrease in the undesired production of the environmentally sensitive byproduct, methyl bromide, can likewise be expected in the practice of the invention.

Figure 4:
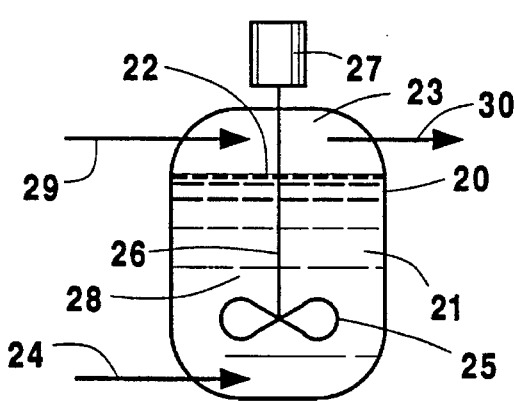
FIG. 4 is a schematic side elevational view of a conventional reactor design that can be employed in evaporative cooling operations of the invention using oxygen in place of air for the oxidation of p-xylene.

It should be noted that, in less preferred embodiments, the substitution of oxygen for air in the oxidation of organic chemicals, e.g. hydrocarbons, can be carried out in conventional reactor vessels operating such as to remove the exothermic heat of the oxidation reaction by evaporation cooling. In FIG. 4 of the drawings, reactor vessel 20 containing a body of liquid reactant 21, with gas-liquid interface 22 and overhead gas phase 23, has oxygen injected therein through line 24. Agitation means 25, driven by drive shaft 26 and drive motor 27, is used to disperse the oxygen in the form of bubbles 28 in said body of liquid reactant 21. Nitrogen or other inert vent gas is introduced into overhead gas phase 23 through line 29, and vent gas is withdrawn therefrom through line 30.

By running the oxidation reaction in reactor vessel 20 at the boiling point of the reaction mixture, i.e., with no excess gaseous oxygen, the heat of reaction of the oxidation reaction is removed from the reaction mixture by evaporative cooling. Under such conditions, many of the advantages observed with oxygen based processing, i.e., increased reaction rate, decreased vent flow, reduction in byproduct formation, are realized. Because the flow patterns are different in systems such as shown in FIG. 4, however, oxygen is not trapped in roll cells, such as those advantageously formed in the LOR embodiment of FIG. 3, and more of the undissolved oxygen escapes into the overhead gas phase. Therefore, the system of FIG. 4 is less oxygen efficient than the FIG. 3 embodiment and requires the use of more nitrogen or other inert gas for safety purposes. Thus, to avoid safety problems associated with dangerous concentrations of oxygen in overhead gas phase 23 in such reactor operations, a large amount of nitrogen or other inert vent gas must be passed to said overhead gas phase 23 to avoid safety problems associated with the presence of excess oxygen in said gas phase. The additional cost of such nitrogen or other gas could well render this embodiment uneconomical from a practical operating viewpoint.

Many of the advantages recited above for the practice of the preferred embodiment of the invention as illustrated in FIG. 3 would be realized in the practice of the less preferred FIG. 4 embodiment, i.e., increased reaction rate, decreased vent flow, reduction in byproduct formation. In addition to the large nitrogen or other inert gas flow to the overhead gas space, the oxygen utilization efficiency of the FIG. 4 embodiment is much lower than for the FIG. 3 embodiments of the invention, or for the embodiments of the Litz patent, because there is no provision for the recirculation of unreacted oxygen, i.e. in the roll cells of the FIG. 3 embodiment. Thus, more oxygen would be required, since more of the oxygen passed to the reactor would be vented unreacted. The additional amounts of oxygen and nitrogen required in the FIG. 4 approach, and the associated costs, render said FIG. 4 embodiment less desirable, and perhaps uneconomical, for various commercial applications of the TPA production operation.

Those skilled in the art will appreciate that various changes and modifications can be made in the details of the invention without departing from the scope thereof as recited in the appended claims. For example, a solvent other than acetic acid, e.g., a monobasic aliphatic acid containing two to four carbon atoms, could be employed. While essentially pure oxygen is advantageously employed in the preferred embodiments of the invention, other nearly pure oxygen-rich gases having a significantly higher oxygen content than air, i.e., oxygen-rich air having at least about 50%, preferably at least about 90%, and up to essentially 100%, oxygen, can also be used in various embodiments of the invention.

As will be seen from the illustrated embodiments, pure oxygen or an oxygen-rich gas is injected directly into the recirculating portion of the body of liquid at an oxygen injection point or points near the impeller means. For purposes of this invention, a position near the impeller means is one within the turbulent flow field produced by the impeller means, including the impeller suction and discharge flow fields. The turbulent flow field also significantly includes the roll cells, i.e. roll cells B in FIG. 3, formed in the reactor vessel below the hollow draft tube and said impeller means.

The invention provides a significant advance in the field of TPA production. The highly effective LOR system is desirably modified for use without cavitation, enabling the desirable LOR gas-liquid mixing process and system to be employed with evaporative cooling. Not only does the practice of the invention enable the LOR process and system to be extended effectively to the oxidation of p-xylene to product TPA solid product, the use of pure or nearly pure oxygen in the practice of the invention enables reaction conditions to be employed such as to reduce undesired byproduct formation, and to reduce solvent consumption and gas throughput in the reaction system and waste gas generation. The evaporative cooling feature of the invention offers significant and unexpected benefits in the increased reduction of liquid reactant and solvent consumption. By enabling by-product and waste generation to be reduced, while enhancing oxygen utilization and enabling milder operating conditions to be employed, the invention provides highly desirable technical, economic and environmental advantage over conventional TPA production operations.

We claim:

1. An improved process for the production of terephthalic acid by the oxidation of p-xylene present in a body of liquid contained within a reactor vessel, without appreciable loss of oxygen to the overhead gas phase, comprising:

(a) maintaining said body of liquid containing p-xylene reactant, an organic solvent, catalyst and a bromine initiator in a recirculating flow pattern by impeller means positioned therein, said body of liquid having a gas-liquid interface with an overhead gas phase;

(b) injecting pure oxygen or an oxygen-rich gas directly into said recirculating portion of the body of liquid at an oxygen injection point or points near said impeller means at a point of high turbulence within the turbulent flow field produced by said impeller means so as to rapidly disperse oxygen in the liquid as small bubbles for rapid consumption of at least about 90% of said oxygen upon injection into the liquid, the heat of reaction due to the oxidation of p-xylene being removed by evaporative cooling upon evaporation of volatile organic material and water present in said body of liquid, with bubbles of said evaporated organic material and water vapor, accompanied by only small quantities of undissolved oxygen, rising upward in said body of liquid through a relatively quiescent, essentially non-turbulent, zone in the upper portion of the reactor vessel to the gas-liquid interface and to said overhead gas phase; and (c) maintaining the oxygen-p-xylene mixture in the reactor vessel at a temperature of from about 150° C. to about 200° C., and a pressure of between 100 psig and 200 psig, for a residence time of from about 30 to about 90 minutes;

(d) venting said bubbles of evaporated organic material and water vapor, accompanied by only small quantities of oxygen, from the overhead gas phase;

(e) recovering terephthalic acid product from the reactor vessel, whereby the oxygen and the p-xylene reactant are mixed under conditions promoting the rapid consumption of oxygen and the evaporation of organic material and water with only small amounts of oxygen bubbles being passed to the overhead gas phase.

2. The process of claim 1 and including passing an inert gas through the overhead gas phase to inert small quantities of oxygen passing to the overhead gas phase.

3. The process of claim 2 in which the recirculating flow pattern is maintained in the body of liquid by an axial flow, downward pumping impeller means positioned in the reactor vessel, the impeller means having an upwardly extending drive shaft with baffle means positioned thereon for preventing the ingestion of gas from the overhead gas phase along said drive shaft and into the liquid passing to said impeller means, the liquid passing downward through said downward pumping impeller means being at a high velocity such as to create high turbulent roll cells that trap undissolved oxygen and enhance the dissolution thereof.

4. The process of claim 3 in which said axial flow, downward pumping impeller means is positioned in the lower portion of an essentially centrally positioned hollow draft tube having open ends at the top and bottom thereof so that the recirculating flow pattern is downward in the hollow draft tube and upward outside thereof, the hollow draft tube having an enlarged, conically flared upper portion extending upward in vertical distance about 0% to about 20% of the length of the bottom portion thereof, said upper portion having an enlarged upper diameter minimizing the downward velocity of liquid across the top of said hollow draft tube.

5. The process of claim 4 in which the oxygen injection point is in the hollow draft tube below said axial flow, downward pumping impeller means.

6. The process of claim 5 in which radial flow impeller means are positioned in said hollow draft tube below said axial flow, downward pumping impeller means, said oxygen injection point being located between the axial flow, downward pumping impeller means and said radial flow impeller means.

7. The process of claim 5 in which radial flow impeller means are positioned in said hollow draft tube below said downward pumping impeller means, said oxygen injection point being below said radial flow impeller means.

8. The process of claim 4 in which the oxygen injection point is below the hollow draft tube.

9. The process of claim 2 in which said body of liquid is maintained at the boiling point of the reaction mixture with no excess gaseous oxygen being present therein.

10. The process of claim 4 in which the enlarged, conically flared upper portion of the hollow draft tube extends upward from about 100% to about 150% of the length of the bottom portion thereof.

11. The process of claim 1 in which said solvent comprises acetic acid, the solvent:p-xylene reactant ratio being from about 1:1 to about 8:1 on a wt/volume basis.

12. The process of claim 11 in which said catalyst comprises a mixture of cobalt and manganese catalysts, with the catalyst loading being between 500 and 3,000 ppm based on the volume of the liquid reaction mixture, the weight ratio of cobalt catalyst to manganese catalyst being from 0.1:1 to 10:1 on a weight basis.

\* \* \* \* \*

UNITED STATES PATENT AND TRADEMARK OFFICE
CERTIFICATE OF CORRECTION

PATENT NO. : 5,523,474

DATED : June 4, 1996

INVENTOR(S) : Jeffrey P. Kingsley; Anne K. Roby

It is certified that error appears in the above-identified patent and that said Letters Patent is hereby corrected as shown below:

In column 6, line 14, delete "20%" and insert therefor -- 200% --

Column 12;

In claim 4, line 8, delete "20%" and insert therefor -- 200% --.

Signed and Sealed this

Twenty-second Day of October, 1996

Attest:

BRUCE LEHMAN

Attesting Officer     Commissioner of Patents and Trademarks